(12) United States Patent
Kelley et al.

(10) Patent No.: US 6,683,159 B2
(45) Date of Patent: Jan. 27, 2004

(54) METHODS FOR PRODUCING FACTOR VIII PROTEINS

(75) Inventors: Brian D. Kelley, Medford, MA (US); Suresh Vunnum, North Andover, MA (US); Johanna Dalborg, Stockholm (SE); Anna Petersson, Enskede (SE)

(73) Assignee: Genetics Institute, LLC, Cambridge, MA (US)

( * ) Notice: Subject to any disclaimer, the term of this patent is extended or adjusted under 35 U.S.C. 154(b) by 358 days.

(21) Appl. No.: 09/752,280

(22) Filed: Dec. 29, 2000

(65) Prior Publication Data

US 2002/0115832 A1 Aug. 22, 2002

Related U.S. Application Data

(63) Continuation of application No. 09/266,322, filed on Mar. 11, 1999, now abandoned.
(60) Provisional application No. 60/077,802, filed on Mar. 12, 1998.

(51) Int. Cl.$^7$ .................. C07K 14/755; C07K 1/18; C07K 1/22
(52) U.S. Cl. .................. 530/383; 530/380; 530/413; 530/414; 530/415; 514/2; 514/12
(58) Field of Search ................ 530/383, 380, 530/413, 414, 415; 514/2, 12

(56) References Cited

U.S. PATENT DOCUMENTS

| | | |
|---|---|---|
| 4,757,006 A | 7/1988 | Toole et al. |
| 4,868,112 A | 9/1989 | Toole |
| 5,470,954 A | 11/1995 | Neslund et al. |

FOREIGN PATENT DOCUMENTS

| | | |
|---|---|---|
| WO | WO 86/04486 | 8/1986 |
| WO | WO 86/06101 | 10/1986 |
| WO | WO 87/04187 | 7/1987 |
| WO | WO 87/07144 | 12/1987 |
| WO | WO 88/03558 | 5/1988 |
| WO | WO 88/08035 | 10/1988 |

OTHER PUBLICATIONS

J. Toole et al., "Molecular Cloning of a cDNA Encoding Human Antihaemophilic Factor," Nature, 312:342–347 (1984).

Wood et al., "Expression of Active Human Factor VIII from Recombinant DNA Clones," Nature, 312:330–337 (1984).

D.N. Fass, et al., "Monoclonal Antibodies to Porcine Factor VIII Coagulant and Their Use in the Isolation of Active Coagulant Protein," Blood, 59:594–600 (1982).

*Primary Examiner*—Christopher S. F. Low
*Assistant Examiner*—Chin-Min Kam

(57) ABSTRACT

Methods are provided for purification of Factor VIII polypeptides by immunoaffinity chromatography and ion exchange chromatography, in which the eluate from the immunoaffinity column is diluted with a solution comprising higher salt concentration, or lower non-polar agent concentration than that of the elution solution, prior to passing the diluted solution through the ion exchange column. The methods result in improved purification without significant yield loss.

8 Claims, No Drawings

METHODS FOR PRODUCING FACTOR VIII PROTEINS

This application is a continuation of Ser. No. 09/266,322, filed Mar. 11, 1999, now abandoned, which claim benefit of No. 60/077,802, filed Mar. 12, 1998.

FIELD OF THE INVENTION

The present invention relates to improved methods for the purification of procoagulant proteins, particularly recombinant production of Factor VIII and related proteins.

BACKGROUND OF THE INVENTION

Hemophilia is an inherited disease which has been known for centuries, but it is only within the last few decades that it has been possible to differentiate among the various forms; hemophilia A and hemophilia B. Hemophilia A is caused by strongly decreased level or absence of biologically active coagulation factor VIII, which is a protein normally present in plasma.

Until recently, therapeutic factor VIII concentrates have been prepared by fractionation of plasma. However, in recent years, DNA sequences encoding the human coagulation cofactor, Factor VIII:C (FVIII), became known in the art [see e.g., Toole et al, 1984, Nature 312:312–317; Wood et al, 1984, Nature 312:330–337; Vehar et al, 1984, Nature 312:337–342], as well as methods for expressing them to produce recombinant FVIII [see e.g. Toole, U.S. Pat. No. 4,757,006; WO 87/04187, WO 88/08035 and WO 88/03558]. Active variants and analogs of FVIII protein, and DNA sequences encoding them, have also been reported [see e.g. Toole, U.S. Pat. No. 4,868,112; EP 0 786 474; WO 86/06101 and WO 87/07144]. Generally, such variants and analogs are modified such that part or all of the B domain are missing and/or specific amino acid positions are modified, for example, such that normally protease-labile sites are resistant to proteolysis, e.g. by thrombin or activated Protein C. Other analogs include modification at one or more lysine and/or tyrosine residues.

It has been previously surprisingly found that the B domain is dispensable for the procoagulant activity of FVIII, and that active procoagulant protein can be expressed and secreted by expression of a FVIII-encoding DNA in which the nucleotide region encoding part or all of the B domain is lacking. Not only is active protein of these variants produced and secreted, it accumulates in the media at higher levels than when expressed by the full-length DNA. The reduced level of active procoagulant FVIII protein in the media has been attributed, at least in part to several factors [see e.g. WO 87/04187, WO 88/08035 and WO 88/03558]. In Toole et al., *Exploration of Structure-Function Relationships in Human Factor VIII by Site-directed Mutagenesis*, Cold Spring Harbor Symposium on Quantitative Biology, 51:543 (1986), it was reported that recombinant FVIII could be purified by a combination of monoclonal antibody affinity chromatography and ion-exchange chromatography. U.S. Pat. No. 5,470,954 describes a similar process in which FVIII is passed directly from immunoaffinity purification to the ion exchange column. In that document it is stated that changing the ionic strength of the eluted polypeptide solution increases the chance that monoclonal antibodies will remain bound to the FVIII polypeptide and co-purify.

SUMMARY OF THE INVENTION

In the present invention, it has been found that diluting the eluate from the monoclonal antibody column provides certain advantages in yield and/or reduced monoclonal antibody contamination of the FVIII protein being purified therefrom. Accordingly, the present invention provides improved methods for the purification of procoagulant proteins, including both FVIII and variants thereof, which may be produced by recombinant techniques in higher yield and/or in more homogeneous form.

The present invention provides improved methods of purification of FVIII protein from cell cultures, preferably from recombinant cell cultures. The methods provide for obtaining FVIII protein of a higher purity than methods currently in use. In one embodiment, the methods of the present invention comprise diluting the eluate from the immunoaffinity column with a solution of higher ionic strength than the eluate solution. In another embodiment, the methods of the present invention comprise diluting the eluate from an immunoaffinity column with a solution containing lower amounts of ethylene glycol than contained in the eluate solution.

DETAILED DESCRIPTION OF THE INVENTION

Accordingly, the present invention provides improved methods for purification of a Factor VIII polypeptide comprising:

a) adding a mixture containing Factor VIII polypeptide to be purified to an immunoaffinity matrix which binds by hydrophobic attraction to the FVIII polypeptide;

b) eluting the Factor VIII polypeptide from the immunoaffinity matrix with a desorbing solution which causes desorption of the Factor VIII polypeptide, which is released in an elution solution;

c) diluting the elution solution with a solution comprising higher ionic strength than that of the elution solution, resulting in a diluted Factor VIII solution;

d) passing the diluted Factor VIII solution through an ion exchange column capable of binding to the Factor VIII polypeptide, thereby binding the Factor VIII polypeptide while allowing contaminants to pass through the ion exchange column; and e) eluting the purified Factor VIII polypeptide from the ion exchange column.

The desorbing solution of step (b) may contain no salt, or very low salt. The dilution of step (c) is preferably performed using a solution comprising from about 5 to about 20 mM NaCl, most preferably about 5 to about 15 mM NaCl. The eluting solution is preferably diluted with salt-containing solution from about 3-fold to about 5-fold, most preferably about 3-fold.

In another embodiment, the present invention comprises improved methods for purification of a Factor VIII polypeptide comprising:

a) adding a mixture containing Factor VIII polypeptide to be purified to an immunoaffinity matrix which binds by hydrophobic attraction to the FVIII polypeptide;

b) eluting the Factor VIII polypeptide from the immunoaffinity matrix with a desorbing solution which causes desorption of the Factor VIII polypeptide, which is released in an elution solution, wherein the desorbing solution comprises a non-polar agent;

c) diluting the elution solution with a solution comprising lower concentration of the non-polar agent than that of the desorbing solution, resulting in a diluted Factor VIII solution;

d) passing the diluted Factor VIII solution through an ion exchange column capable of binding to the Factor VIII polypeptide, thereby binding the Factor VIII polypeptide while allowing contaminants to pass through the ion exchange column; and e) eluting the purified Factor VIII polypeptide from the ion exchange column.

Preferably, the desorbing solution of step (b) contains ethylene glycol, more preferably about 50% (v/v) ethylene glycol, and the dilution of step (c) is performed using a solution comprising less than about 50% (v/v) ethylene glycol, such that the final concentration of ethylene glycol is from about 17% to about 33% (v/v). In a preferred embodiment, the desorbing solution of step (b) contains 50% (v/v) ethylene glycol, and the dilution of step (c) is performed using a solution comprising no ethylene glycol, such that the final concentration of ethylene glycol is from about 17 to about 33% (v/v), most preferably about 33% (v/v) ethylene glycol. Preferably, the elution solution is diluted from about 1.5-fold to about 3-fold, most preferably about 1.5 fold, or 2:3.

The Factor VIII polypeptide of the present invention is generally produced recombinantly, but may also be purified from plasma. The recombinant Factor VIII polypeptide may be natural full length Factor VIII polypeptide, or a variant, such as a B-domain deleted variant of Factor VIII, including the VIII:SQ variant.

The immunoaffinity columns useful in the present invention may be any industrially acceptable column and resin, to which is adsorbed one or more monoclonal or polyclonal antibodies which are capable of binding to a Factor VIII polypeptide and in which the Factor VIII polypeptide may later be released using standard methods and reagents. Suitable monoclonal antibodies, for example, are disclosed in Fass et al., *Blood,* 59:594–600 (1982).

Useful as the desorbing substance is any non-polar agent, such as ethylene glycol, dioxane, propylene glycol and polyethylene glycol, or any appropriate low ionic strength, low polarity buffered solution.

In preferred embodiments, the mixtures containing Factor VIII polypeptides may also include detergents and/or solvents, such as polyoxyethyl detergents, including Triton X-100, Tween 80. In addition, the Factor VIII polypeptide containing solution may include buffering substances, such as histidine.

EXAMPLE 1
Preparation of Recombinant Factor VIII:SQ

The production of recombinant factor VIII:SQ (r-VIII SQ) was essentially performed as described in patent WO-A-9109122, [examples 1–3]. A DHFR deficient CHO cell line (DG44NY) was electroporated with an expression vector containing the r-VIII SQ gene and an expression vector containing the dihydrofolate reductase gene. The conditioned medium (containing fetal calf serum) was clarified and then concentrated by tangential flow filtration. The solution was loaded onto an SP Sepharose Fast Flow cation exchange resin, wherein the r-VIII SQ binds selectively to the resin through electrostatic forces.

The r-VIII SQ is eluted from the column at elevated ionic strength by flowing elution solution (0.8 M NaCl, 3 mM EDTA, 0.02% (v/v) surfactant [Octoxynol 9], 0.1 MNH$_4$Ac, 5 mM CaCl$_2$, 1 M Sorbitol, pH 6.3±0.2) and is collected as a single UV adsorbing peak. The r-VIII SQ is then put through a virus inactivation step employing the solvent/detergent method using TNBP [Tri-(n-butyl)phosphate] and surfactant [such as Octoxynol 9, Triton X-100).

The r-VIII SQ is next loaded onto an immunoaffinity chromatography gel, where the ligand was a monoclonal antibody (mAb, named 8A4) directed towards the heavy chain of factor VIII. After washing, the factor VIII was eluted with a buffer containing 0.05 M histidine, 0.05 M CaCl$_2$ and 50% ethylene glycol and 0.02% Octoxynol 9 (Tween), pH 6.6. The mAb eluate was loaded onto an anion exchange column, Q Sepharose® FF sold by Pharmacia AB of Uppsala, Sweden. After washing, the FVIII SQ was eluted with a Q elution buffer containing 0.05 M histidine, 4 mM CaCl$_2$ 0.4 M NaCl, pH 6.3.

In order to improve upon the above purification system, several series of experiments were conducted to evaluate the effects on FVIII recovery of (a) dilution; (b) dilution with added NaCl; and (c) dilution with reduced, or with no, ethylene glycol.

Q Equilibration Buffer

The solution used to equilibrate the Q-column (the same as the desorption buffer of the monoclonal antibody column) prior to loading onto the ion exchange column comprises approximately the following composition:

0.05 M histidine 0.05 M calcium chloride

50% (v/v) ethylene glycol 0.02% (v/v) Octoxynol 9 or other surfactant pH 6.6±0.2

Series 1: Dilution with Q Equilibration Buffer

Following immunoaffinity purification, the eluate was diluted from about 3-fold to about 5-fold with Q-equilibration buffer. In the 3-fold dilution, total recovery of FVIII activity was acceptable, though reduced, while murine IgG detected in the eluate was very low. At higher dilutions, the loss of yield of FVIII activity was significant.

Series 2: Dilution with Q Equilibration Buffer Containing NaCl

Following immunoaffinity purification, the eluate was diluted from about 3-fold to about 5-fold with Q-equilibration buffer containing NaCl in the range of about 7 to about 20 mM. Dilution generally produces a significant reduction in the amount of murine IgG recovered from the eluate prior to placing on the ion exchange column. Surprisingly, the addition of NaCl also increased recovery of FVIII activity. This increase in recovery was sufficient to offset the loss in recovery resulting from dilution. The best results were observed in 3-fold to 5-fold dilutions with NaCl in the range of about 10 to about 17 mM NaCl. The best recovery yields of FVIII activity were obtained with dilutions of about 3-fold with about 15 mM NaCl. Dilution with less than about 7 mM NaCl or greater than about 20 mM NaCl resulted in a loss of final recovery of FVIII activity.

The conclusion is that addition of about 7 mM to about 20 mM NaCl to the Q Equilibration Buffer used to dilute the immunoaffinity eluate restores the loss of yield associated with dilution without NaCl, while also producing beneficial results by reducing the murine antibody detected in the eluate. In the most preferred embodiment, addition of Q Equilibrium Buffer with about 15 mM NaCl added produced optimal results.

Series 3 and 4: Dilution with Q Equilibration Buffer with no or Reduced Ethylene Glycol Following immunoaffinity purification, the eluate is diluted from about 1.5-fold to about 3-fold with Q Equilibration Buffer that does not contain ethylene glycol, resulting in final ethylene glycol content varying from about 50% (v/v) in the Q Equilibration Buffer down to as low as about 17% (v/v) in the 3-fold dilution without ethylene glycol. A 1.5-fold dilution without ethylene glycol resulted in about a 33% (v/v) final ethylene glycol concentration. With decreased ethylene glycol concentration, total recovery of protein increased over comparable dilution with Q Equilibration Buffer containing about 50% (v/v) ethylene glycol.

EXAMPLE 2

1.0 Introduction

A suitable downstream purification process for Factor VIII:SQ as produced in Example 1 may consist of five chromatographic steps: cationic exchange (SP Sepharose FF), immunoaffinity (mAb Sepharose FF), anionic exchange (Q Sepharose FF), hydrophobic interaction (HIC, butyl Sepharose FF), and gel permeation chromatography (Superdex 200 pg). The eluate from the mAb column may be directly loaded onto Q-Sepharose FF column. A series of loading conditions on Q-Sepharose FF column was examined by PPD (in collaboration with P&U, Stockholm) to (I) study the impact of the loading conditions on the activity recovery and the reduction in mouse IgG and HCP levels in the Q-Sepharose peak pool; (ii) establish optimal loading conditions on the anion exchanger. Results of this study are summarized in this Example.

2.0 Experimental Procedures 2.1 Materials:

Q-Sepharose FF resin was packed in a 79×5 mm ID Pharmacia HR column. All buffers employed in this study were prepared by CTS by established procedures. The mAb peak pool from the purification process were obtained frozen at −80° C. from P&U, Stockholm (LtE 923). The COBAS assay kit and mega standard was bought from Chromogenix AB, Sweden.

2.2. Procedures:

Q-Sepharose Scale Down Runs:

The Q-Sepharose FF column was initially equilibrated with 10 CV of buffer at a flow rate of 0.5 ml/min. Subsequently, the mAb peak pool was diluted with the appropriate dilution buffer and loaded onto the Q-Sepharose FF column at a flow rate of 0.2 mil/min. The total activity units loaded in all the experiments was 48,350 U/ml of the resins and is close to the upper limit specified in the PLA. The activity of the mAb peak pool used to perform these experiments was 2860 IU/ml. The load volume in the 3-fold and 5-fold dilution experiments was therefore 78.6 mls and 131 mls respectively. Following the load, the column was washed with 40 CVs of a buffer containing 150 mM NaCl, 4 mM $CaCl_2$, 50 mM Histidine, pH 6.6, at a flow rate of 0.32 ml/min (wash 2). The bound protein was then eluted with a buffer containing 400 mM NaCl, 4 mM CaCl2, 50 mM Histidine, pH 6.3 at a flow rate of 0.05 ml/min. Wash 2 and elution in all the experiments were performed at a flow rate of 0.05 ml/min. Wash 2 and elution in all the experiments were performed in the reverse direction. The column effluent during the various operations was collected and assayed for activity. A 1.6 cv fraction was pooled during elution beginning at the upward drift in the absorbance at 280 nm and is termed the peak pool. The load and peak pool samples were assayed for mouse IgG and HCP levels by performing ELISA (P&U, Stockholm).

Regeneration:

The anion exchange column was regenerated, following each scale down run, by passing five column volumes each of 2.0 M NaCl, 100 mM sodium phosphate (monobasic), pH 3.0 and 2.0 M NaCl, 100 nM sodium phosphate (dibasic), pH 11.0.

Time Course Stability Studies:

The mAB peak pool was diluted different fold with (I) mAb elution buffer and (ii) mAb elution buffer containing 40 mM NaCl, and incubated at room temperature. The activity in these samples was then assayed at different time points.

3.0 Results and Discussions

Time Course Stability Study:

The mAB peak pool was diluted 2-fold, 3-fold and 5-fold with mAB elution buffer and incubated at room temperature. The drop in activity of these samples was monitored as a function of time. A modest drop of 20% in activity was observed over the course of 24 hours. The loss in activity was negligible at the end of 4 hours, and less than 10% at the end of 8 hours. Further, percentage drop in activity was observed to be independent of the extent of dilution of the mAb peak pool and hence independent of the solution concentration of FVIII in the mAb elution buffer. Similar results were obtained upon dilution of the mAb peak pool with mAb elution buffer containing 40 mM NaCl.

Q-Sepharose Scale Down Experiments:

Results from the scale-down runs of the Q-Sepharose FF column performed with the mAb peak pool diluted 3-fold and 5-fold with the mAb elution buffer is shown in Table 1.

TABLE 1

Dilution with mAb Elution Buffer

| Dilution Fold | Challenge (IU/ml resin) | Load (IU/ml) | Loading Time (hours) | Load Activity at End of Run (% of Initial Activity) | Flow Through Loss (%) |
|---|---|---|---|---|---|
| 3 | 48,350 | 953 | 6.55 | 82.8 | 3.6 |
| 5 | 48,350 | 572 | 10.9 | 70.4 | 3.3 |

| Dilution Fold | Wash #1 (%) | Wash #2 (%) | Pre-Peak (%) | Peak (1.6 cv)(%) | Post-Peak (%) | Total Recovery |
|---|---|---|---|---|---|---|
| 3 | 0.7 | 0.1 | <0.1 | 57.4 | 3.9 | 65.8 |
| 5 | 0.4 | 0.1 | <0.1 | 41.3 | 2.5 | 47.7 |

The flow-through losses in both cases was approximately 3.5% of the load, while the combined activity losses in the wash and prepeak samples were less then 1%. The activity in the 1.6 cv peak pool for the 3- and 5-fold dilution experiments were 57.5% and 41.3%, respectively, of the load, while the post-peak accounted for 3.9 and 2.5% of the load activity units, respectively. The corresponding values in manufacturing runs, wherein the mAb peak pool was loaded onto the column with no further modification of the eluate, is 5% in the flow-through and 70±9% in the peak pool. The other effluent streams have negligible activity.

These results clearly demonstrate that the yield across the Q-Sepharose FF column is sensitive to the extent of dilution of the mAb peak pool prior to loading onto the column, and decreases with increasing dilution. However, it is evident from the time course stability studies that solution stability of FVIII:SQ is not affected by dilution. For a fixed number of activity units loaded onto the column, the operating time increases with dilution. As suggested by the time course stability data, a drop in yield can therefore be expected at higher load dilutions. Nevertheless, experimentally obtained activity values from the scale down runs was significantly lower than supported by the time course stability data. One possible explanation is that the adsorption of FVIII:SQ onto the Q-Sepharose resin under dilute conditions leads to stronger interaction with the resin and has a denaturing effect on the protein, thereby leading to a lower recovery upon elution. The yield at higher dilutions could then be improved by attenuating the 'FVIII:SQ-resin' interaction during loading. In order to test this hypothesis, subsequent experiments were performed with the mAb peak pool diluted with mAb elution buffer containing NaCl.

Dilution with mAb Elution Buffer Containing NaCl:

The results from the Q-Sepharose scale down experiments performed using mAb peak pool diluted with mAb elution buffer containing various concentrations of NaCl is shown in Table 2.

in the presence of NaCl. The maximum overall and peak activity recovery was obtained at a NaCl concentration of 15 mM. However, existence of an optimum NaCl concentration is not as evident at this dilution level as it was at 5-fold dilution.

TABLE 2a

5-Fold Dilution With mAb Elution Buffer Containing NaCl

| Load NaCl Conc (mM) | Challenge (IU/ml resin) | Load (IU/ml) | Loading Time (hours) | Load Activity at End of Run (% of Initial Activity) | Flow Through Loss (%) |
|---|---|---|---|---|---|
| 10 | 48,350 | 572 | 10.9 | 90.3 | 6.5 |
| 10 | 48,350 | 572 | 10.9 | 85.8 | 6.8 |
| 15 | 48,350 | 572 | 10.9 | 76.4 | 6.6 |
| 20 | 48,350 | 572 | 10.9 | 73.3 | 6.9 |
| 20 | 48,350 | 572 | 10.9 | 88.9 | 8.5 |

| Load NaCl Conc | Wash #1 (%) | Wash #2 (%) | Pre-Peak (%) | Peak (1.6 cv) (%) | Post-Peak (%) | Total Recovery |
|---|---|---|---|---|---|---|
| 10 | 0.8 | 0.2 | <0.1 | 73.1 | 1.8 | 82.4 |
| 10 | 0.9 | 0.2 | <0.1 | 71.8 | 3.4 | 83.1 |
| 15 | 0.9 | 0.1 | — | 61.0 | 7.3 | 75.9 |
| 20 | 0.9 | 0.2 | — | 49.8 | 12.4 | 70.3 |
| 20 | 1.0 | 0.2 | — | 46.3 | 20.1 | 76.1 |

TABLE 2b

3-Fold Dilution With mAb Elution Buffer Containing NaCl

| Load NaCl Conc. (mM) | Challenge (IU/ml resin) | Load (IU/ml) | Loading Time (hours) | Load Activity at End of Run (% of Initial Activity) | Flow Through Loss (%) |
|---|---|---|---|---|---|
| 7 | 48,350 | 953 | 6.55 | 94.4 | 5.5 |
| 10 | 48,350 | 953 | 6.55 | 86.3 | 6.0 |
| 12.5 | 48,350 | 953 | 6.55 | 91.6 | 9.1 |
| 16.7 | 48,350 | 953 | 6.55 | 82.0 | 6.5 |

| Load NaCl Conc. | Wash #1 (%) | Wash #2 (%) | Pre-Peak (%) | Peak (1.6 cv)(%) | Post-Peak (%) | Total Recovery |
|---|---|---|---|---|---|---|
| 7 | 1.3 | 0.1 | — | 58.3 | 9.9 | 75.1 |
| 10 | 1.3 | 0.1 | — | 79.9 | 3.2 | 90.5 |
| 12.5 | 2.1 | 0.6 | — | 58.8 | 12.0 | 82.5 |
| 16.7 | 1.7 | 0.4 | — | 59.3 | 4.7 | 72.6 |

5-fold Dilution Experiments:

Loading the diluted mAb peak pool under conditions that attenuate the 'FVIII:SQ-resin' interaction significantly increased the overall activity recovery across the Q-Sepharose column. A greater fraction of this increase in activity was seen in the peak pool for the runs employing 10 and 15 mM NaCl in the load, suggesting that there exists an optimal NaCl concentration that leads to a maximum peak activity recovery.

In the NaCl concentration range of about 7 to 20 mM, the activity loss in the flow through varied between 6.5 and 8.5%. These values are twice of that seen in the 5-fold dilution run in the absence of NaCl. The combined wash and prepeak activity losses in all cases were less than 2%. The activity losses in the post-peak pool increases with increasing NaCl concentration and was as high as 20% at an NaCl concentration of 20 mM. This is expected since the protein migrates farther down the column during loading and subsequently takes longer to elute when the flow is reversed.

3-Fold Dilution:

As in the case of 5-fold dilution, the overall activity recovery and flow-through losses were higher when loaded Mouse IgG Results:

The mouse IgG data on the peak and post-peak pools for all 3- and 5-fold dilution experiments are shown in Table 3:

TABLE 3

Mouse IgG Data from 3-Fold and 5-Fold Dilution Experiments

| Diluition Fold | Load NaCl Concentration | IgG Levels in Peak Pool (ng/KIU) | IgG Levels in Post-Peak Pool (ng/KIU) |
|---|---|---|---|
| 3-fold | 0 | 0.8 | 2.1 |
|  | 7 | 0.5 | 2.0 |
|  | 10 | 0.8 | 5.3 |
|  | 12.5 | 0.7 | 1.8 |
|  | 16.7 | 1.2 | 3.6 |
| 5-fold | 0 | 0.5 | 2.1 |
|  | 10 | 0.8 | 3.2 |
|  | 10 | 0.8 | 3.6 |
|  | 15 | 0.7 | 2.3 |
|  | 20 | 0.4 | 1.5 |
|  | 20 | 0.6 | 1.3 |

The IgG values in the peak pool for the 3-fold dilution runs varied from 0.5 to 1.2 ng/KIU and 0.5 to 0.8 ng/KIU for the 5-fold dilution runs. The corresponding values in manufacturing runs, wherein the mAb peak pool was loaded onto the column with no further modification of the eluate, averaged 2.3 ng/KIU. Thus, dilution of the mAb peak pool with mAb elution buffer, with or without NaCl, prior to loading reduced the IgG levels in the Q-Sepharose peak pool. This effect, beyond the mere dilution of IgG levels, may be the result of a given association constant for formation of IgG-FVIII:SQ complex. Thus, lowering the concentrations of IgG and FVIII:SQ lowers the concentration of the complex, thereby allowing greater removal of IgG across the ion exchanger. In both the 3-fold and 5-fold dilution experiments, no correlation was observed between IgG values in the Q-Sepharose peak pool and NaCl concentrations in the load. Thus, in the range of NaCl concentrations employed in these experiments, addition of NaCl does not appear to provide additional reduction in mouse IgG levels.

Host Cell Protein Results:

The host cell protein data on the peak pool for the 3-fold and 5-fold dilution experiments are shown in Table 4:

TABLE 4

Host Cell Protein (HCP) Levels in 3-Fold and 5-Fold Dilution Experiments

| Dilution Fold | Load NaCl Conc (mM) | HCP in Peak Pool (ng/KIU) |
|---|---|---|
| 3 | 7 | 10.3 |
|   | 12.5 | 4.2 |
| 5 | 10 | 14.1 |
|   | 15 | 9.9 |
|   | 20 | 10.9 |

The corresponding values in manufacturing runs, wherein the mAb peak pool was loaded onto the column with no further modification of the eluate, averaged 20 ng/KIU. These results suggest that the HCP levels in the peak pool decrease with increasing NaCl concentrations, and are independent of the extent of dilution. The addition of NaCl may attenuate the binding of HCP to the resin, and therefore allow lower levels of HCP in the Q-Sepharose peak pool.

4.0 Conclusions

Dilution of the mAb peak pool with mAb elution buffer prior to loading on Q-Sepharose column significantly decreased the yield across this step. The decrease in yield is an increasing function of the extent of dilution. However, the solution stability of FVIII is independent of the extent of dilution with mAb elution buffer, thereby suggesting that loading under dilute conditions leads to a stronger 'FVIII-resin' interaction and has a denaturing effect on the protein. Addition of sodium chloride to the dilution buffer attenuates the 'FVIII-resin' interaction and increases the yield across the Q-Sepharose column. Increasing the NaCl concentrations, however, increases the flow-through and post-peak losses and hence there exists an optimum NaCl concentration at which the yield losses are significantly offset. The optimum concentration for the 3-fold and 5-fold dilution runs appears to be in the 7 to 20 mM concentration, more particularly about 15 mM.

Diluting the mAb peak pool with mAb elution buffer also reduced the IgG and HCP levels in the Q-Sepharose peak pool. In the concentration range of NaCl examined, HCP levels in the Q-Sepharose peak pool decreased with increasing NaCl concentrations in the load. Overall, a combination of dilution of the mAb peak pool and adding NaCl at concentrations of 7 to 20 mM resulted in improved purification without significant yield loss.

What is claimed is:

1. A method for purification of a Factor VIII polypeptide comprising:
    (a) adding a mixture containing a Factor VIII polypeptide to be purified to an immunoaffinity matrix which binds the Factor VIII polypeptide by hydrophobic attraction;
    (b) eluting the Factor VIII polypeptide from the immunoaffinity matrix with an elution solution which desorbs the Factor VIII polypeptide;
    (c) diluting the elution solution about 3-fold to about 5-fold with a solution comprising higher NaCl concentration than that of the elution solution, resulting in a diluted Factor VIII solution comprising about 7–20 mM NaCl;
    (d) passing the diluted Factor VIII solution through an ion exchange column which binds the Factor VIII polypeptide, thereby allowing contaminants to pass through the ion exchange column; and
    (e) eluting the purified factor VIII polypeptide from the ion exchange column.

2. The method of claim 1, wherein the elution solution of step (b) contains no NaCl salt.

3. The method of claim 1, wherein the elution solution of step (b) contains no NaCl salt, and the diluted Factor VIII solution in step (c) comprises about 15 mM NaCl.

4. The method of claim 3, wherein the elution solution is diluted about 3-fold.

5. A method for purification of a Factor VIII polypeptide comprising:
    (a) adding a mixture containing a Factor VIII polypeptide to be purified to an immunoaffinity matrix which binds the Factor VIII polypeptide by hydrophobic attraction;
    (b) eluting the Factor VIII polypeptide from the immunoaffinity matrix with an elution solution which desorbs the Factor VIII polypeptide, wherein the elution solution comprises a non-polar agent, and wherein the non-polar agent comprises at least on of ethylene glycol, dioxane, propylene glycol and polyethylene glycol;
    (c) diluting the elution solution about 1.5-fold to about 3-fold with a solution comprising lower concentration of the non-polar agent than that of the elution solution, resulting in a diluted Factor VIII solution comprising about 17% to about 33% (v/v) non-polar agent;
    (d) passing the diluted Factor VIII solution through an ion exchange column which binds the Factor VIII polypeptide, thereby allowing contaminants to pass through the ion exchange column; and
    (e) eluting the purified Factor VIII polypeptide from the ion exchange column.

6. The method of claim 5, wherein the elution solution of step (b) contains 50% (v/v) ethylene glycol, and the dilution of step (c) is performed using a solution comprising less than 50% (v/v) ethylene glycol, such that the final concentration of ethylene glycol in the diluted factor VIII solution is from about 17% to about 33% (v/v).

7. The method of claim 5, wherein the elution solution of step (b) contains 50% (v/v) ethylene glycol, and the dilution of step (c) is performed using a solution comprising no ethylene glycol, such that the final concentration of ethylene glycol in the diluted factor VIII solution is from about 17% to about 33% (v/v).

8. The method of claim 7, wherein the elution solution is diluted about 1.5-fold.

* * * * *